(12) United States Patent
Wiles et al.

(10) Patent No.: US 6,509,964 B2
(45) Date of Patent: Jan. 21, 2003

(54) MULTI-BEAM APPARATUS FOR MEASURING SURFACE QUALITY

(75) Inventors: Gregory R. Wiles, Royal Oak, MI (US); Charles C. Prain, III, Oxford, MI (US)

(73) Assignee: AMT Inc., Madison Heights, MI (US)

( * ) Notice: Subject to any disclaimer, the term of this patent is extended or adjusted under 35 U.S.C. 154(b) by 37 days.

(21) Appl. No.: 09/858,205

(22) Filed: May 15, 2001

(65) Prior Publication Data

US 2002/0171826 A1 Nov. 21, 2002

(51) Int. Cl.[7] .............................................. G01N 21/00
(52) U.S. Cl. ..................... 356/237.2; 356/446; 356/445; 356/600
(58) Field of Search ................................ 356/600, 446, 356/445, 237.2

(56) References Cited

U.S. PATENT DOCUMENTS

| | | | |
|---|---|---|---|
| 3,574,469 A | 4/1971 | Emerson | 356/200 |
| 3,748,047 A | 7/1973 | Millgard et al. | 356/200 |
| 3,840,303 A | 10/1974 | Clarke | 356/200 |
| 3,898,469 A | 8/1975 | Nichols et al. | 250/563 |
| 4,085,322 A | 4/1978 | Sick | 250/227 |
| 4,110,047 A | 8/1978 | Takahashi | 356/200 |
| 4,139,307 A | 2/1979 | Clarke | 356/446 |
| 4,265,545 A | 5/1981 | Slaker | 356/431 |
| 4,445,126 A | 4/1984 | Tsukada | 346/108 |
| 4,527,898 A | 7/1985 | Stapleton | 356/446 |
| 4,746,805 A | 5/1988 | Stapleton | 250/571 |
| 4,761,676 A | 8/1988 | Wiles et al. | 356/445 |
| 4,904,877 A * | 2/1990 | Pietzsch | 250/572 |
| 4,933,568 A | 6/1990 | Dippel et al. | 250/572 |
| 4,989,984 A | 2/1991 | Salinger | 356/445 |
| 5,072,114 A | 12/1991 | Takada | 250/235 |
| 5,087,822 A | 2/1992 | Fairlie et al. | 250/572 |
| 5,229,835 A * | 7/1993 | Reinsch | 356/371 |
| 5,315,321 A | 5/1994 | Peled et al. | 346/108 |
| 5,552,890 A * | 9/1996 | Nanna et al. | 356/369 |
| 5,570,183 A * | 10/1996 | Wiles | 356/371 |
| 5,686,731 A | 11/1997 | Wiles et al. | 250/559.22 |
| 6,104,481 A * | 8/2000 | Sekine et al. | 356/237.5 |
| 6,122,042 A * | 9/2000 | Wunderman et al. | 356/73 |
| 6,215,551 B1 * | 4/2001 | Nikoonahad et al. | 356/237.2 |
| 6,266,138 B1 * | 7/2001 | Keshavmurthy | 356/237.2 |
| 6,317,204 B2 * | 11/2001 | Haga et al. | 356/237.2 |

* cited by examiner

Primary Examiner—Michael G. Lee
Assistant Examiner—Ahshik Kim
(74) Attorney, Agent, or Firm—Gifford, Krass, Groh, Sprinkle, Anderson & Citkowski, P.C.

(57) ABSTRACT

An apparatus for measuring the visual characteristics of a surface of a workpiece includes two separate light sources. The first source provides one or more focused beams of light which strike the workpiece at a first angle and are reflected therefrom. The second source provides one or more unfocused beams of light which strike the workpiece at a second angle, different from the first angle, and are reflected therefrom. All of the reflected beams converge onto a single photo detector. The beams are time multiplexed so that the photo detector only reads one beam at a time. The output of the photo detector is processed to provide surface quality measurements of the workpiece such as gloss, distinctness of image and orange peel.

45 Claims, 4 Drawing Sheets

MULTI-BEAM APPARATUS FOR MEASURING SURFACE QUALITY

FIELD OF THE INVENTION

This invention relates generally to surface inspection and characterization systems. More specifically, the invention relates to optical based, surface measuring systems in which a plurality of beams of light are directed onto a workpiece for reflection therefrom.

BACKGROUND OF THE INVENTION

It is often necessary to measure the surface characteristics of painted, plated, polished or otherwise finished objects in the course of their manufacture. The visual appearance of a finished surface is a highly subjective determination; however, a number of parameters have been established in the art to quantify aspects of surface quality. Among the measurements which are commonly made are: distinctiveness of image (DOI), which is a measure of how clearly an object is reflected by a surface; gloss, which is a measurement of the dispersion with which light is reflected from a surface; and orange peel, which is a surface characteristic dependent upon the presence of a repeating pattern of surface features having a texture in the general size range of 0.5 to 1.0 millimeter, and which produce a texture appearing somewhat reminiscent of the skin of an orange. Other parameters which are sometimes measured include tension, which is a measurement of the clarity with which a projected grid pattern is reflected from a surface, and haze (also referred to as texture), which is a measurement of the clarity with which the image of an object is reflected from the surface. There is overlap in the quantities which are measured by these various determinations, and various manufacturers will rely upon different ones of these parameters for quality control purposes. In some instances, these surface quality parameters are assessed subjectively by comparing a finished surface with a series of standards. In other instances, various algorithms have been developed for calculating these parameters, based upon the reflection of light from the surface. For example, some particular techniques for the measurement of gloss and distinctiveness of image are disclosed in U.S. Pat. Nos. 4,761,676; 4,746,805 and 4,527,898.

In a manufacturing environment, automated systems are often utilized for quantifying the aforementioned parameters. Such systems require accuracy, ease of use, high speed operation, mechanical simplicity and low cost; however, these parameters are often mutually exclusive. Accuracy generally requires that a relatively large area of a workpiece be measured so as to produce a representative reading of its properties. However, using one single, large area light beam to read the workpiece produces errors, since the large beam will fail to read small area features and can also introduce sampling errors. For example, orange peel readings are very difficult to automate. Orange peel results from the presence of relatively small features, which repeat at differing frequencies. If a large area beam is used to measure orange peel, it will fail to read relatively small features; but, if a small diameter beam is utilized for orange peel measurements, it cannot provide an accurate reading unless it is scanned over a relatively large area. As a consequence, the prior art has typically raster scanned a measuring beam across a relatively large area of a workpiece in order to obtain surface quality measurements. Such scanning is slow, and requires complicated hardware.

The prior art has implemented a number of approaches to improving automated surface quality measurements, and various of these approaches are found in U.S. Pat. Nos. 5,570,183; 5,686,731 and 4,989,984. In some instances, multiple beams are employed for scanning a surface, and such approaches are shown in U.S. Pat. Nos. 4,265,545 and 4,110,047. Prior art systems tend to be expensive, mechanically complex and slow in operation. Accordingly, there is a need for an optical inspection system which, in addition to being accurate, is fast in operation and simple in construction. As will be explained in detail hereinbelow, the present invention provides a surface quality measuring system which utilizes a plurality of light sources segregated into two distinct groupings. Use of a number of sources simplifies the optical system of the device and minimizes sampling times. In addition, the system of the present invention utilizes a time multiplexed detection system which eliminates redundancy in parts and improves the reliability and operating speed of the device. These and other advantages will be apparent from the drawings, discussion and description which follow.

BRIEF DESCRIPTION OF THE INVENTION

There is disclosed herein an apparatus for measuring the visual characteristics of a surface of a workpiece. The apparatus includes a first light source which is operative to direct at least one focused beam of light onto the workpiece for reflection therefrom and a second light source operative to direct at least one unfocused beam of light onto the surface of the workpiece for reflection therefrom, at a location separate from the location at which the first beam or beams impinge the workpiece. The system also includes a photo detector which produces a signal in response to illumination, means for directing the first and second sets of reflected beams of light onto the photo detector, and a multiplexer for causing the photo detector to sequentially detect each member of the first and second sets of reflected beams so that the photo detector produces a separate signal corresponding to each of the reflected beams. The system can further include a signal processor which processes data from the photo detector and generates readings of surface quality such as DOI, orange peel and gloss.

In particular embodiments, the first light source directs a plurality of focused beams of light onto the workpiece and the second source directs a single unfocused beam onto the workpiece. The light sources may comprise diode lasers, and in particular embodiments, the beams from the first source are directed onto the workpiece at the Brewster angle for that wavelength and workpiece material. Illumination at the Brewster angle maximizes surface reflection thereby avoiding interference from metal flakes and other such subsurface reflective bodies.

In another aspect of the present invention, a light source of the apparatus includes a plurality of separate light emitters, each light emitter operative to direct a single beam of light onto a different portion of the surface of a workpiece, at a common angle of incidence for reflection therefrom. In this embodiment, the light emitters are disposed in an angled relationship to one another so that the beams of light therefrom follow paths which are converging as they approach the surface. The paths meet at a convergence point following reflection. Most preferably, a photo detector is disposed at the convergence point, and in this manner, a single photo detector can receive and read all of the beams. Multiplexing of the beams allows for signal separation.

DETAILED DESCRIPTION OF THE INVENTION

The present invention provides an apparatus for measuring the visual characteristics of a surface. Such characteristics can include distinctness of image, gloss and orange peel, as well as other measurements such as haze and tension. It is to be understood that data generated through the use of the apparatus of the present invention may be processed, in accord with various techniques known in the art, so as to generate still other optical measurements of surface quality. It is a notable feature of the present invention that the apparatus includes first and second light sources. Each source includes at least one light emitter which directs a beam of light onto the surface being measured. It is further notable that the first light source provides one or more beams of focused light and the second provides one or more beams of unfocused light. Further in accord with the present invention, all beams of light from the two sources are reflected off the surface being measured and ultimately directed onto a single photo detector. Through the use of a single detector, the size, complexity and cost of the apparatus is reduced. In accord with the present invention, multiplexing is utilized to assure that the detector provides separate signals for each of the beams of light striking it. Multiplexing is typically accomplished by selectively activating the light sources in rapid sequence.

Figure 1:
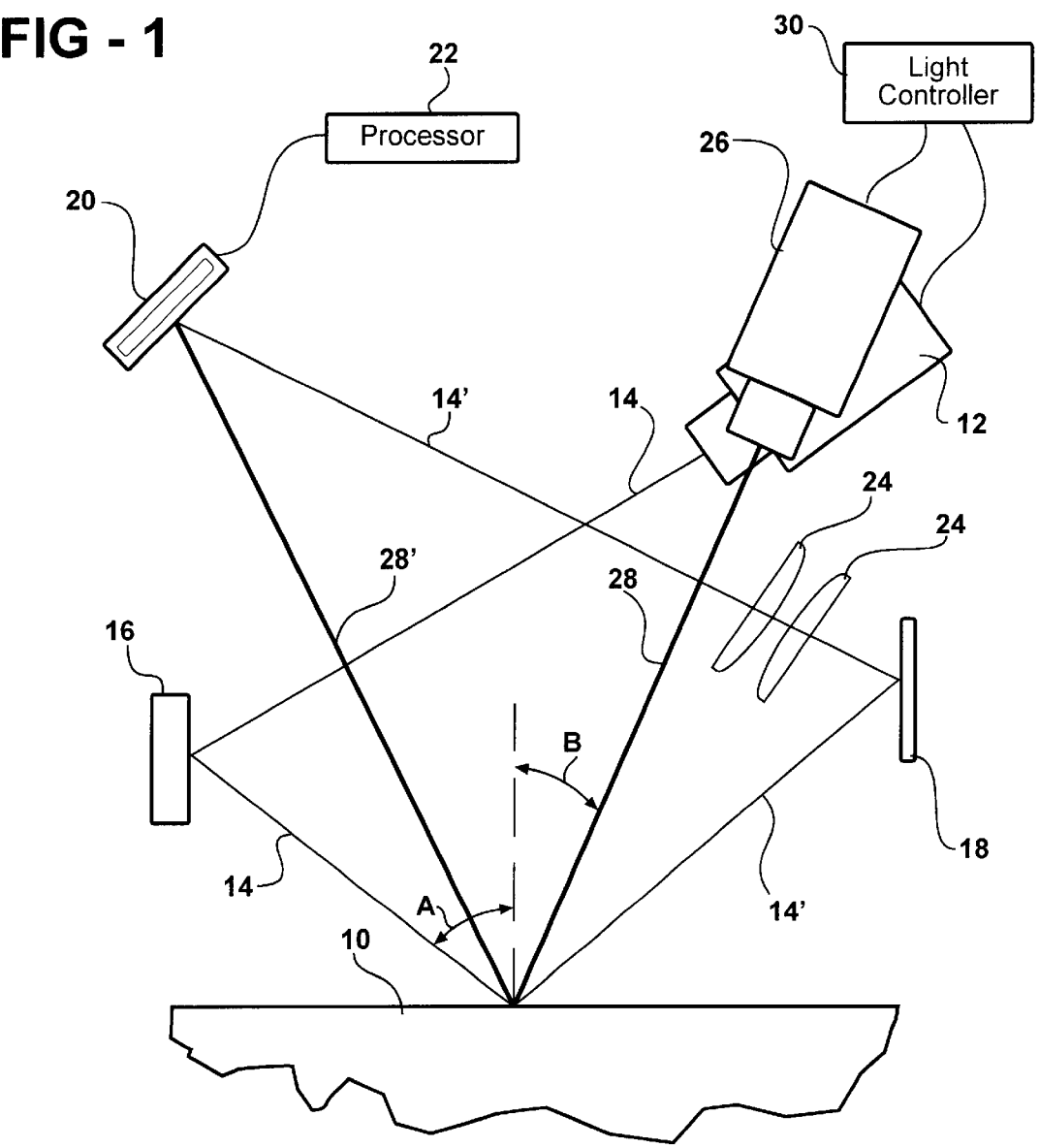
FIG. 1 is a simplified schematic depiction of the optical system of the present invention.

The invention will be further explained with reference to FIG. 1, which comprises a simplified schematic depiction of an optical system of the present invention. The system of FIG. 1 is shown as being employed to measure the visual characteristics of a workpiece 10. The system includes a first light source 12 which is operative to direct a beam 14 of focused light onto the surface of the workpiece 10. As shown in FIG. 1, the first light source 12 is depicted as comprising a single light source; however, in preferred embodiments of the present invention, the first light source has a plurality of separate light emitters, each operative to generate a separate beam of focused light which is impinged onto the workpiece. However, the principles of the present invention are equally applicable to single beam light sources, and for the sake of clarity will be explained in this context with regard to FIG. 1. The focused beam of light 14 impinges onto a first mirror 16 and is subsequently directed to the workpiece 10 where it is reflected so as to produce a reflected beam 14' which strikes a second mirror 18 which redirects the beam 14' to a photo detector 20. The photo detector generates a signal in response to illumination, and this signal can be processed in the data processor 22 so as to provide information on the visual characteristics of the surface of the workpiece 10. In this regard, the photo detector 20 can include a plurality of separate segments so as to produce an output signal representative of the spatial distribution of the reflected light. Thus, in the context of this disclosure, a "single photo detector" is understood to include a detector comprised of an array of photoresponsive segments, as well as a detector having only one photoresponsive element. As further shown in FIG. 1, the system can include lenses 24 or other such optical elements to aid in directing the selected light beam 14' onto the detector 20. It is also to be understood that the mirrors 16, 18 and lenses 24 can be eliminated if the light source and detector are appropriately repositioned; however, by employing such optical elements, the path of the light can be folded so as to decrease the size of the measuring apparatus.

As previously mentioned, light from the first source 12 is focused so as to produce a relatively small spot on the workpiece 10. It is also preferable that the beam of light 14 from the first source 12 be directed so as to strike the workpiece surface 10 at an angle, indicated by arrow A, which approximates the Brewster angle for that particular wavelength of light and index of refraction of the surface material of the workpiece 10. As is known in the art, light striking a surface at the Brewster angle, also referred to as the polarization angle, is most strongly reflected from the surface with little, if any, component being reflected from subsurface portions of the workpiece. By so directing light, subsurface reflections, as for example from metal flakes, pigment particles and the like are eliminated, thereby giving an accurate reading of surface quality. For a typical surface finished with automotive grade paint, utilizing a focused beam having a wavelength of approximately 670 nanometers, the angle of incidence A is approximately 56.4°.

The system of FIG. 1 further includes a second light source 26, which is disposed to provide a beam of unfocused light 28 which is impinged onto the surface of the workpiece 10 to provide a reflected beam 28' which strikes the photo detector 20. The unfocused beam 28 is preferably a collimated beam, and it strikes the workpiece 10 at an angle indicated by arrow B which, in this embodiment, is approximately 20°. The 20° geometry is preferably employed, since many optical measurement standards are established on the basis of a 20° beam. Since the beam 28 is unfocused, it is of relatively large diameter, most typically in the range of 0.1–3 millimeters; hence, minor subsurface imperfections have a relatively small effect on this beam, and Brewster angle geometry is not required.

It will be noted that the incident beam 28 and the reflected beam 28' pass from the second light source 26 to the detector 20 without any intervening optical elements. It is to be understood that in some instances, mirrors, lenses and other such beam directing elements may be included in the optical system in order to shorten the optical path or otherwise redirect beams 28, 28', and such is within the scope of the present invention.

As will be seen from FIG. 1, the present invention provides a very compact geometry wherein a plurality of light beams (typically four from the first source and one from the second source) are directed onto the workpiece and reflected therefrom. The reflected beams are all converged onto the same point on a single photo detector 20. This simplifies optical geometry and avoids the need for utilizing several detectors. Further in accord with the present invention, multiplexing is used to assure that the detector 20 only generates a single signal at any one time, which signal is representative of a single one of the beams. This is most preferably accomplished by utilizing a light source controller 30 to sequentially energize each of the light emitters in the light sources so that a series of beams, separated in time, are produced. The detector 20 receives these time separated beams and generates time separated signals, which are conveyed to the processor 22. The source controller 30 and processor 22 are preferably in communication so that the processor 22 can identify which beam is being detected at any particular time.

It is generally preferred that the various beams of light be scanned across the surface of the workpiece in the course of making measurements. It will be appreciated from FIG. 1 that scanning of all beams can be easily accomplished by translating light sources 12, 26, mirrors 16, 18 and photo detector 20 as a single unit, relative to the surface of the workpiece. The fact that the geometry of the system permits all of these components to be rigidly joined together greatly simplifies the scanning system. As will be noted, no rotating mirrors or other separately movable optical elements are required. The fact that the system includes a plurality of beams, allows a large area of the workpiece to be measured in a single pass thereby avoiding the need for raster scanning. Furthermore, the fact that all optical elements are fixed relative to one another greatly increases the reliability and ruggedness of the system.

In accord with another preferred, but not required, feature of the present invention, individual light emitters comprising a given light source are oriented relative to one another so that the beams of light emitted thereby travel on paths which converge. The convergence point is located downstream of the points at which the beams are reflected from the workpiece surface, and most preferably at the photo detector. While this converging path geometry is not necessary, by so positioning the light emitters, the optical system is further simplified.

Figure 2:
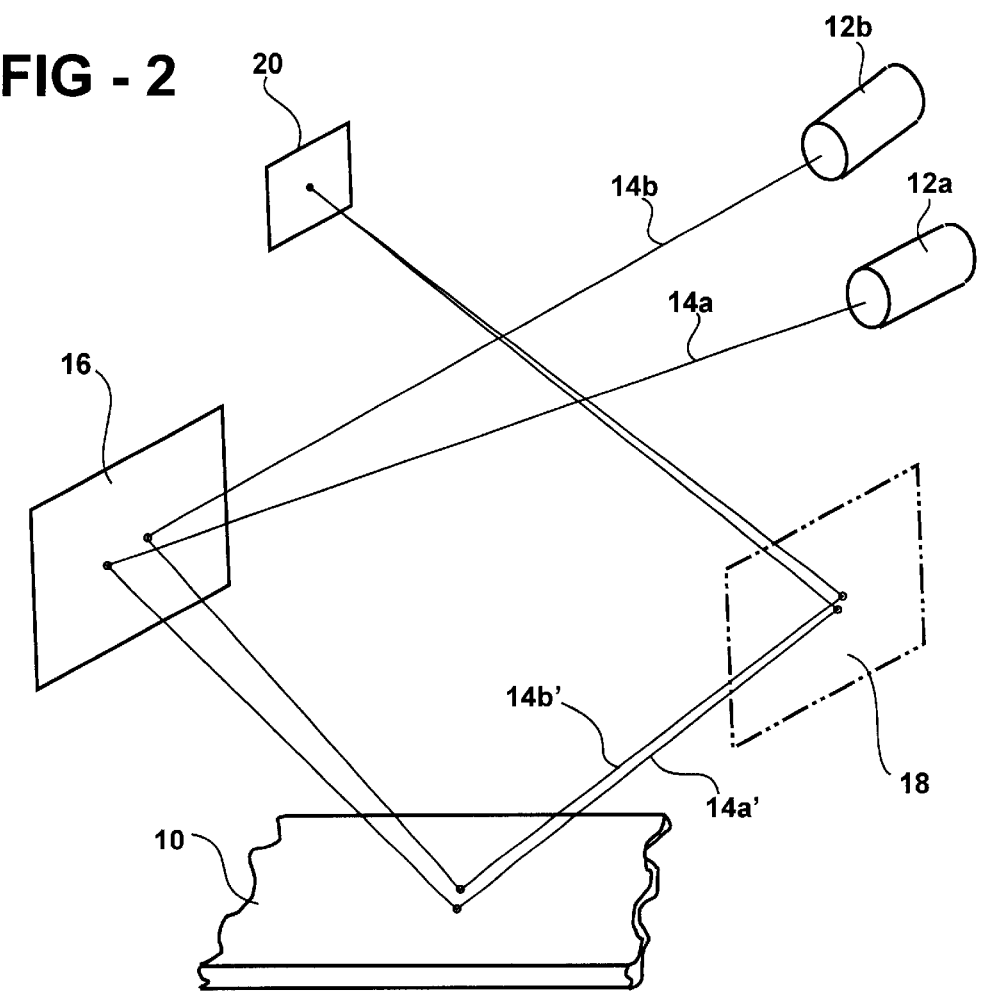
FIG. 2 is a perspective view of a schematic depiction of converging light beams from two light emitters of the present invention, shown as impacting onto a single photo detector.

Referring now to FIG. 2, there is shown a schematic depiction, in perspective, of portions of an optical system in accord with the present invention, and generally similar to that of FIG. 1. The depicted system of FIG. 2 includes two light emitters 12a, 12b which comprise the first light source. These emitters each provide a focused beam of light 14a, 14b which is directed onto the workpiece 10 by a first mirror 16. As will be seen, the two beams 14a, 14b are converging as they approach the first mirror 16, and continue to converge as they approach the workpiece 10. Beams 14a, 14b are reflected from the workpiece, and the reflected beams 14a', 14b' are further converging as they approach the second mirror 18 (which is shown herein in phantom outline). The reflected beams 14a', 14b' continue to converge and strike the photo detector 20 at approximately the same point. It is to be understood that other light emitters may be similarly disposed in the system, and oriented so that their beams likewise converge at the same point on the detector 20. It should be noted that in the FIG. 2 schematic depiction, for purposes of clarity, the second light source and its beam are not illustrated. It is to be understood that this second light source is disposed so as to also reflect its beam of light onto the common point on the photo detector 20. In one presently preferred commercial embodiment, the first light source includes four separate emitters oriented so as to produce four converging beams. This embodiment includes a second light source which provides a single unfocused beam; although, in other embodiments, the second light source can also include a plurality of beams, in which instance, the convergent geometry shown in FIG. 2 may be advantageously employed.

Figure 3:
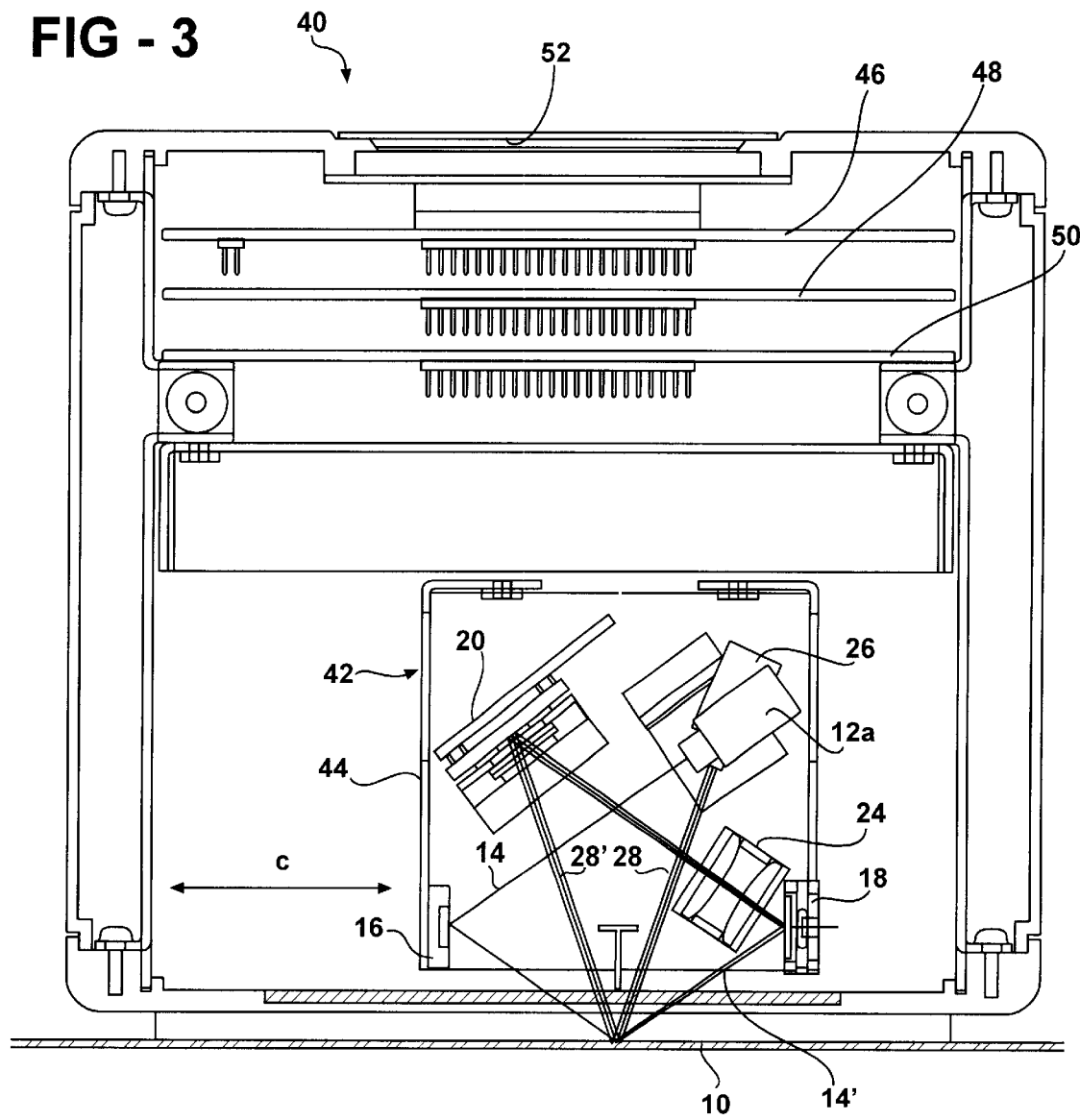
FIG. 3 is a cutaway view, in elevation, of one embodiment of multi-beam apparatus structured in accord with the principles of the present invention.

Referring now to FIG. 3 there is shown a cutaway view, in elevation, of one commercial embodiment of measuring apparatus structured in accord with the principles of the present invention. The apparatus 40 of FIG. 3 includes an optical system 42 which is supported on movable support 44, with the various elements thereof rigidly affixed relative to one another. The optical system includes a first light source 12 which, in this embodiment, is comprised of four photo diodes, one of which, 12a, is visible, the others being aligned there behind. The photo diodes comprise laser diodes emitting light at approximately 670 nanometers, and such laser diodes are available from the Coherent Corporation of Auburn, Calif. As previously described, the first light source directs focused beams of light 14 onto the surface of a workpiece 10. The diameter of each focused beam is approximately 0.5 mm. As illustrated, the beams 14 are reflected from a first mirror 16 onto the workpiece 10, and then again reflected by a second mirror 18 so as to converge at a single point on a photo detector 20. In the illustrated embodiment, the second mirror 18 comprises an array of individually adjustable mirrors, each of which is disposed to receive one of the reflected beams 14' from the first source 12. It has been found that by making the mirrors individually adjustable, the reflected beams 14 may be more readily directed to the same convergence point on the detector 20. As discussed above, a lens assembly 24 is further employed to adjust the convergence point of the reflected beams 14. It is preferable that the intensities of the focused beams comprising the first source are all relatively equal. Beam intensity can be adjusted by controlling the power applied to each emitter; however, it has been found that intensities can be readily equalized by interposing a polarizer in each beam. Thus by rotating either the polarizer or the laser, the intensity of the beam (which is polarized at the emitter) can be adjusted.

In the illustrated embodiment, the second light source 26 comprises a single laser photo diode of the type previously described; however, this laser photo diode is configured to provide a beam of collimated, unfocused light. It is to be understood that within the context of this invention, an unfocused beam of light is a beam of light which does not converge onto a focal point. It is further understood that a collimated beam of light may be regarded as a beam of light having a focal point at infinity; however, for purposes of this discussion, a collimated beam of light is considered an unfocused beam of light since it does not have a tangible focal point. In the illustrated embodiment, the single laser photo diode of the second source is disposed between second and third photo diodes of the first source. As illustrated, the collimated, unfocused beam of light from the second source 26 impinges on the workpiece at an approximate 20° angle and is directly reflected on the photo detector 20. The diameter of the unfocused beam is approximately 2 millimeters.

In the illustrated embodiment, the frame 44 of the optical assembly 42 is mechanically translatable as indicated by double headed arrow C. This enables the beams of light from the first and second sources to be swept across the workpiece so as to make the rapid scanning of a relatively large area. Scanning is preferably accomplished by use of a motor drive and worm screw, not shown, although other drive systems known in the art may be similarly employed. As further illustrated, the apparatus 40 includes a plurality of circuit boards 46, 48, 50. These boards support the electronic circuitry for controlling and driving the operation of the system, and for sequentially activating laser diodes so as to produce a time multiplexed light output, and for calculating visual characteristics of the surface of the workpiece. In this illustrated embodiment, the light emitters are sequentially activated to produce pulses of approximately 800–900 microsecond duration, and approximately 1024 distinct readings are taken in the course of a three inch scan. In the illustrated embodiment, a visual display, comprising a liquid crystal display unit 52, is disposed on the top surface of the apparatus 40 and functions to display measured parameters.

In the illustrated embodiment, the beams of focused light from the first source 12 are preferably utilized to calculate the orange peel characteristics of the workpiece surface. The source provides for spaced apart beams, having relatively small diameter. These beams scan the surface of the workpiece, and data therefrom, as provided by the photo detector 20, is converted to orange peel readings. The unfocused beam from the second source 26 is used to calculate gloss and distinctness of image. Signal processing for calculation of the parameters may be by any of the methods known in the art. In accord with another aspect of the present invention, there is provided a specifically preferred methodology for calculating surface quality parameters.

Figure 4:
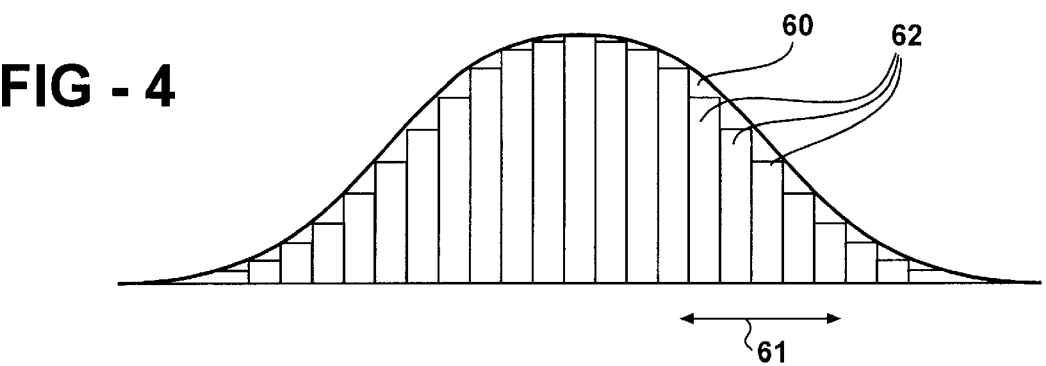
FIG. 4 is a plot of the spatial distribution of light intensity as measured using the present invention.

FIG. 4 is a plot of light intensity 60 measured by the detector 20 as a function of spatial distribution 61. Although a smoothly varying curve would be optimum, the plot is stair-stepped (62) due to the use of the discrete devices forming the detector array 20. This quantization does not present a problem however, due to high resolution of modern integrated detector arrays. In fact, in a commercial implementation of the invention, only half of an available 72 array elements are utilized for detection purposes.

Figure 5:
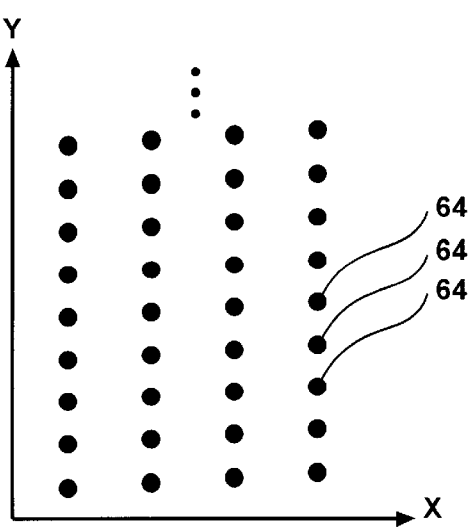
FIG. 5 is a plot showing scan points as measured on a workpiece surface through the use of the present invention.

FIG. 5 is a simplified plot which illustrates a scanned area using the apparatus described elsewhere herein. The x-axis is defined by the spacing of the various light emitters 12 and 26, whereas the y dimension is defined by the movement of the optical assembly 42 within the housing of the instrument. According to a practical implementation, 1,024 samples are gathered per laser with respect to a 3-inch scan area, and the lasers are time-multiplexed as the optical components are translated such that only one laser is activated at a given time. To sample the roughly 4000 points, a conversion is required at a rate of at least twice the frequency of interest according to Nyquist sampling. Since the carriage holding the optical assembly 42 is preferably translated at a substantially constant speed and the emitters are multiplexed, the result is the pattern of skewed dots 64 depicted in FIG. 5.

A bell-shaped curve of the type shown in FIG. 4 is generated and analyzed with respect to each point 64 shown in FIG. 5. According to a preferred method aspect of the invention, the curve developed with respect to each illuminated point is used for multiple purposes. In particular, a central area under the curve, as described below, is used to measure gloss. The area under a different region, or regions, of the same curve is used to measure DOI. For orange peel, a power distribution curve is generated using a Fourier transformation step.

A more detailed description of each process will now be presented, beginning with the gloss and DOI measurements. Reference is made to the bell-shaped curve of FIG. 4, keeping in mind that the gloss (and DOI) measurement is obtained using an unfocused, preferably collimated beam (28), striking the surface under investigation at an angle of 20° off normal. This angle is used because the gloss is preferably measured according to the ASTM 523 standard. This standard mandates "field stops" which are ±0.3° on either side of a specular reflection, which corresponds to a 20° off-normal reflection.

In contrast to previous methods, which use optical blocking arrangements to physically implement the field stops, the invention advantageously simulates the field stops through software which determines where the field stops should be on either side of the peak of the curve as depicted in FIG. 4. In terms of hardware, it is determined how many photodiodes of the detector array 20 should be used to emulate the field stop under the ASTM 523 standard. Importantly, however, since the field stops are synthesized as opposed to permanent, a gloss measurement may be realized according to the invention even if the curve is shifted due to a localized imperfection.

Figure 6:
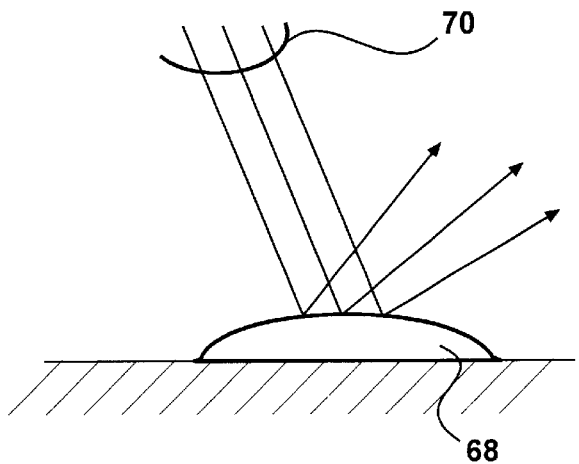
FIG. 6 is a stylized depiction of an imperfection on a workpiece surface being measured through the use of the present invention.

Such a localized imperfection is depicted with numerical reference 68 in FIG. 6. The presence of such a relatively small detail on the surface complicates the field stop determination since, if light rays 70 happens to impinge upon the imperfection, the reflection could produce a false indication of 20±0.3° off normal. Assuming a spot size on the surface on the order of 1500 microns, since orange peel variations are typically larger than this, clearly such imperfections must be taken into account when calculating a weighted-center value. Accordingly, the preferred method performs an intermediate step of calculating the exact center of the curve using, for example, a weighted average to find the center of the distribution. Conveniently, since a number of readings are taken, should one or more measurements be inconsistent, the data may be disregarded in favor of relevant distribution values, for gloss and DOI.

Once the center is located, the process looks to 0.3° on either side of the center to locate the stops. In the event that one or both of the stop positions fall between adjacent photodiodes, the preferred method further interpolates the values measured with respect to the adjacent detectors to ensure an accurate reading. Since the peak of the curve is determined prior to each calculation, curve shifting is normalized and the information gathered by the detector array is still useable for gloss and DOI measurements, a situation which would not be possible using physical field stops.

Having determined the peak intensity value and the points corresponding to ±0.3° off center, the area under the curve (i.e., the integral) between these boundaries is calculated to determine gloss. The determination of DOI is relatively straightforward, since a synthesized "slit" just outside of the 0.3° boundary on either side of the peak may be used for the calculation. Again, this slit is not a physical slit, but rather, a virtual window on either side of each 0.3° boundary. The area under the curve with respect to each window is determined through integration, and preferred correlated to a standard DOI rating as defined by Hunter Labs.

To determine the orange peel, the center of the displacement of the distribution is measured. Broadly, a plurality of sample measurements are gathered, and a Fourier transformation is performed to obtain a distribution curve. The area under this curve is determined by way of integration to obtain a power spectra indicative of orange-peel effect. More particularly, the power spectra of the multiple focused sources are examined as the carriage holding the optical assembly 42 is translated relative to the surface under investigation. Referring back to FIG. 5, these readings may be angled or skewed relative to the surface due to the multiplexing of the various light emitters.

Figure 7:
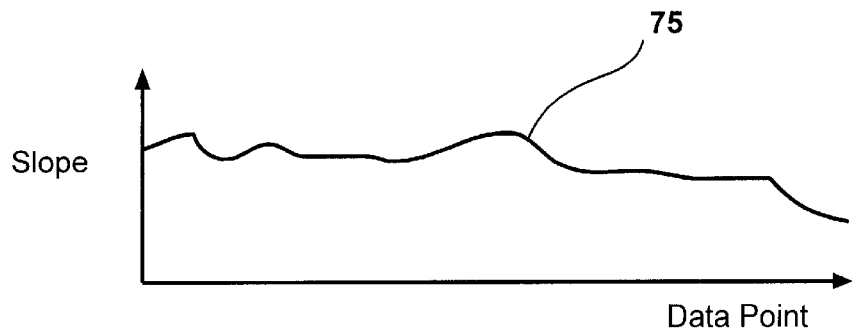
FIG. 7 is a plot of the slope of the displacement of a reflected light beam at various data points as measured in accord with the present invention, which plot is indicative of the surface profile of the workpiece.
Figure 8:
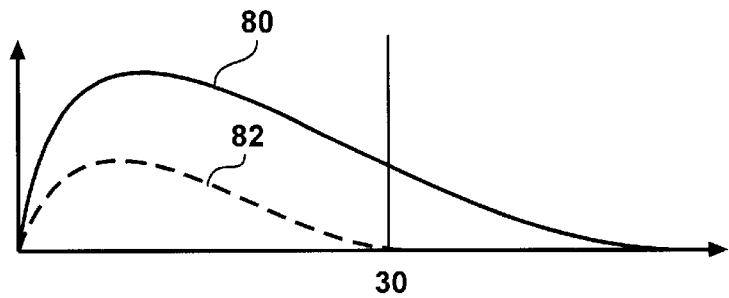
FIG. 8 is a power spectrum as generated in accord with the present invention.

As the surface is traversed, a direct profile 75 is obtained, as shown in FIG. 7, which is a plot of slope as a function of the multiple data points. A fast Fourier transform (FFT) is then performed on the measured values to obtain a power spectra, as depicted in FIG. 8. The power spectra, which plots the transformed values as a function of distance, represents an approximation of human perception in relation to the orange-peel effect. The area under the curve is then computed for a given number, and this value is input as indicative of orange peel.

Two curves 80 and 82 are depicted in FIG. 8. With respect to curve 80, it will be noted that vast majority of the surface imperfections lie within a distance of 30 or below. Accordingly, this number is input as representative of the orange-peel value. In contrast, the broken line 82 represents a very smooth surface indicative of "black glass," wherein there are practically no values beyond a distance of 30.

By way of a summary, this invention always measures gloss, regardless of surface structure, because a weighted center is correlated regardless of the angle of reflection. Even in the presence of a surface modulation which might cause the angle to depart from the desired 20±0.3°, a weighted center is nevertheless formulated, enabling the area under the curve to be calculated without having to discard the gloss or DOI readings. In addition, although prior-art techniques perform gloss and DOI calculations with respect to a single point, these previous approaches consider a much larger surface area with respect to the calculation.

In departing from this methodology, the subject invention instead uses a plurality of localized points which are quite spaced apart across the surface being characterized. As such, this invention effectively measures gloss on the surface even if "bumps" are present; that is, the measured values are lowered due to the existence of a bumpy surface. This invention also effectively "recycles" the slope used to measure orange peel by reading the obtained values back, at least into the DOI reading. The DOI measurement taken according to the invention is actually so superior to results generated using existing techniques that a "de-rating" step is preferably used to ensure agreement to industry standards.

While the foregoing methodology has been described with reference to the specific apparatus of the present invention, the methodology is not so limited, and may be implemented with other apparatus. Such other applications will be apparent to one of skill in the art.

Yet other configurations of apparatus may be similarly structured in accord with the principles of the present invention. It is to be understood that the figures are meant to illustrate some specific embodiments of the present invention but ate not meant to be limitations upon the practice thereof. For example, the number of light sources may be varied from those shown herein. Likewise, the geometry of the optical system, and the numbering and placement of the elements thereof, may be similarly varied. Signals developed through the use of the present invention may be processed in various manners to extract other surface characteristics of the measured workpiece. It is to be understood that the optical system of the present invention may be incorporated as a subsystem in other devices. In view of the foregoing it is to be understood that the drawings, discussion and description presented herein are illustrative of the invention but not meant to be limitations upon the practice thereof. It is the following claims, including all equivalents, which define the scope of the invention.

What is claimed is:

1. An apparatus for measuring the visual characteristics of a surface of a workpiece, said apparatus comprising:

a first light source operative to direct at least one focused beam of light onto a surface of a workpiece for reflection therefrom so as to produce a first set of reflected beams, each beam of said first set corresponding to one of said at least one focused beams;

a second light source operative to direct at least one unfocused beam of light onto said surface of said workpiece for reflection therefrom, at a location separate from a location at which each of said at least one focused beams are directed onto said workpiece, so as to produce a second set of reflected beams, each beam of said second set corresponding to one of said at least one unfocused beams;

a photo detector operative to produce a signal in response to illumination thereof;

means for directing said first and second sets of reflected beams of light onto said photo detector; and multiplexing means for causing said photo detector to sequentially detect each member of said first and second sets of reflected beams, whereby said photo detector produces a separate signal in response to each of said reflected beams.

2. The apparatus of claim 1, wherein said first light source is operative to direct a plurality of focused beams of light onto said surface of said workpiece.

3. The apparatus as in claim 2, wherein said first light source includes a plurality of diode lasers, each diode laser being operative to provide one of said plurality of beams of light.

4. The apparatus of claim 2, wherein said first light source is operative to direct each member of said plurality of beams onto the surface of the workpiece at a different location thereon.

5. The apparatus of claim 1, wherein said first light source is operative to direct said at least one focused beam of light onto said surface of said workpiece at an angle of incidence which is the Brewster angle for said light and for said workpiece.

6. The apparatus of claim 1, wherein said first light source is operative to direct said at least one focused beam of light onto the surface of said workpiece at an angle of incidence which is in the range of 50–60° from normal.

7. The apparatus of claim 1, wherein said angle of incidence is 56.4°.

8. The apparatus of claim 1, wherein said at least one unfocused beam of light comprises at least one collimated, unfocused beam of light.

9. The apparatus of claim 1, wherein said second light source is operative to direct one beam of collimated, unfocused light onto said surface of said workpiece.

10. The apparatus of claim 9, wherein said beam of collimated, unfocused light has a diameter in the range of 1–3 millimeters.

11. The apparatus of claim 1, wherein said second light source is operative to direct said at least one unfocused beam of light onto said surface at an angle of incidence which is in the range of 0–25° from normal.

12. The apparatus of claim 11, wherein said angle of incidence is 20° from normal.

13. The apparatus of claim 1, wherein said means for directing said first and second sets of reflected beams includes a set of mirrors for directing said first set of reflected beams.

14. The apparatus of claim 1, wherein said second light source is operative to direct only one beam of unfocused light onto said surface of said workpiece, whereby said second set of reflected beams includes only one beam; and wherein, said means for directing said first and second sets of reflected beams includes a support for said second light source which positions said second light source so that said one beam of unfocused light is reflected from said workpiece directly onto said photo detector.

15. The apparatus of claim 1, wherein said multiplexing means is a controller operable to sequentially activate said first and second light sources so that each of said at least one focused beam and said at least one unfocused beam are separated in time.

16. The apparatus of claim 1, wherein said first light source is operative to direct a plurality of focused beams of light onto said surface, said first light source including a plurality of diode lasers, each laser being operable to emit one of said focused beams, and wherein said second light source is operative to direct one collimated unfocused beam of light onto said surface, said second light source including one diode laser which is operable to emit said collimated unfocused beam; and wherein said multiplexing means comprises a controller operable to sequentially activate said diode lasers so that said plurality of focused beams and said collimated, unfocused beam are separated in time.

17. The apparatus of claim 1, wherein said photo detector comprises an array of photo diodes.

18. The apparatus of claim 1, wherein said array is a one-dimensional array.

19. The apparatus of claim 1, further including a signal processor in communication with said photo detector, said signal processor operative to receive the signals generated by the photo detector and to process said signals so as to determine a visual characteristic of said surface.

20. The apparatus of claim 1, further including a scanner for scanning said at least one focused beam of light across said surface of said workpiece.

21. The apparatus of claim 20, wherein said scanner is further operative to scan said at least one unfocused beam of light across said surface of said workpiece.

22. In an apparatus for measuring the visual characteristics of a surface of a workpiece, wherein said apparatus includes a plurality of light emitters, each being operative to direct a single beam of light onto a different portion of the surface of the workpiece at a common angle of incidence for reflection therefrom, the improvement comprising in combination:

said light emitters being disposed in an angled relationship to one another so that said beams follow paths which are converging as they approach said surface, said paths meeting at a convergence point after reflection from said surface.

23. The apparatus of claim 22, further including a photo detector disposed at said convergence point.

24. An apparatus for measuring the visual characteristics of a surface of a workpiece, said apparatus comprising:

a first light source operative to direct a plurality of focused beams of light onto different portions of a surface of a workpiece, at a first, common angle of incidence, for reflection therefrom so as to produce a set of reflected, focused beams, each corresponding to one of said focused beams;

a second light source operative to direct a collimated, unfocused beam of light onto said surface at a second angle of incidence, which differs from said first angle of incidence, for reflection therefrom so as to produce an unfocused, reflected beam;

scanning means for scanning said focused beams and said unfocused beam across the surface of the workpiece;

a photo detector operative to produce a signal in response to illumination thereof;

means for directing said reflected focused beams and said reflected unfocused beam onto the same portion of said photo detector; and multiplexing means for causing said photo detector to sequentially detect each of said reflected beams.

25. A method of measuring one or more surface characteristics with respect to a workpiece, comprising the steps of:

directing a beam of light onto a surface of the workpiece so that the light is reflected thereby;

detecting the light reflected by the surface using an array of detector elements to obtain a curve representative of the spatial intensity of the reflected light;

finding the peak of the curve;

determining points on the curve relative to the peak of the curve which are representative of predetermined field stops; and integrated one or more regions under the curve between a pair of the field stops, to produce a signal that corresponds to the surface characteristic being measured.

26. The method of claim 25, wherein the beam of light is directed onto the surface of the workpiece at a predetermined angle of incidence.

27. The method of claim 26, wherein the predetermined angle of incidence is 20°.

28. The method of claim 25, wherein the curve representative of the spatial intensity of the reflected light is a generally bell-shaped curve.

29. The method of claim 25, wherein:

the field stops are located at the same predetermined distance from the peak on either side of the curve; and the measured characteristic is surface gloss.

30. The method of claim 29, wherein:

the light is incident upon the surface at a predetermined angle of 20°; and the field stops are representative of points which are ±0.3° from the peak of the curve.

31. The method of claim 30, further including the steps of:

finding additional points representative of slits just outside the points which are ±0.3° from the peak of the curve; and integrating the areas under the curve within each slit to determine distinctiveness of image.

32. The method of claim 25, wherein:

the field stops are representative of a slit on one side of the curve at a predetermined distance from the peak; and the measured characteristic is distinctiveness of image (DOI).

33. The method of claim 25, wherein the peak of the curve is found through a weighted averaging.

34. The method of claim 25, wherein the beam of light is unfocused.

35. The method of claim 25, wherein the beam of light is collimated.

36. The method of claim 25, further including the steps of:

illuminating a plurality of spaced-apart points on the surface to obtain a direct profile of the surface of the workpiece;

performing a fast Fourier transform on the direct profile to obtain a power spectra curve which plots transformed values as a function of distance;

integrating the area under the curve for a given distance; and comparing the result to a value stored in a look-up table to determine orange peel associated with the surface of the workpiece.

37. A method of measuring surface gloss and distinctiveness of image (DOI) with respect to the surface of a workpiece, comprising the steps of:

directing a beam of unfocused, collimated light onto the surface of the workpiece at a predetermined angle of incidence;

detecting the light reflected by the surface using an array of detector elements to obtain a generally bell-shaped curve representative of the reflected light;

finding the peak of the curve;

determining a first set of points which are representative of predetermined field stops located at the same distance from the peak on either side of the curve;

integrated the area under the curve within the field stops to produce a signal indicative of gloss;

finding additional points representative of slits just outside the field stops; and integrating the areas under the curve within each slit to produce a signal indicative of DOI.

38. The method of claim 37, wherein:

the light is incident upon the surface of the workpiece at a predetermined angle of 20°; and the field stops are representative of points which are 0.3° from the peak of the curve.

39. The method of claim 37, wherein the peak of the curve is found through a weighted averaging.

40. The method of claim 37, further including the steps of:

illuminating a plurality of spaced-apart points on the surface to obtain a direct profile of the surface;

performing a fast Fourier transform on the direct profile to obtain a power spectra curve which plots transformed values as a function of distance; and integrating the area under the curve for a given distance to produce a signal indicative of orange peel.

41. A method of measuring multiple characteristics with respect to the surface of a workpiece, comprising the steps of:

illuminating a plurality of spaced-apart points on the surface using at least one non-focused beam of light at a first predetermined angle of incidence, and at least one focused beam of light at a second predetermined angle of incidence;

detecting the light reflected by the surface using the same array of detector elements to obtain a generally bell-shaped curve representative of the light reflected at each point;

a) when the non-focused beam of light is used to illuminate the surface, performing the following steps:

finding the peak of the curve, determining a first set of points which are representative of predetermined field stops located at the same distance from the peak on either side of the curve, integrated the area under the curve within the field stops as a measure of gloss, finding additional points representative of slits just outside the field stops, and integrating the areas under the curve within each slit to produce a signal indicative of DOI; and b) when the focused beam of light is used to illuminate the surface, performing the following steps:

storing measurements using the light reflected with respect to a plurality of points to obtain a direct profile of the surface, performing a fast Fourier transform (FFT) on the direct profile to obtain a power spectra curve which plots transformed values as a function of distance, and integrating the area under the curve for a given distance to produce a signal indicative of orange peel.

42. The method of claim 41, wherein:

the first predetermined angle of incidence is 20° off surface normal; and the field stops are representative of points which are 0.3° from the peak of the curve.

43. The method of claim 41, wherein the second predetermined angle of incidence is related to the wavelength of the focused beam.

44. The method of claim 43, wherein the wavelength of the focused beam is 670 manometers, and the second predetermined angle of incidence is approximately 56.4°.

45. The method of claim 43, wherein the peak of the curve is found through a weighted averaging.

\* \* \* \* \*